US 6,666,359 B2

(12) United States Patent
Lau et al.

(10) Patent No.: US 6,666,359 B2
(45) Date of Patent: Dec. 23, 2003

(54) CONTROLLED-DOSE DISPENSER WITH INTEGRAL NOZZLE AND CAP

(75) Inventors: Steven Lau, Singapore (SG); Michael Goh, Singapore (SG); Peter W. Heyman, Florham Park, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 180 days.

(21) Appl. No.: 09/876,544

(22) Filed: Jun. 7, 2001

(65) Prior Publication Data

US 2001/0027301 A1 Oct. 4, 2001

Related U.S. Application Data

(63) Continuation of application No. 09/417,344, filed on Oct. 14, 1999.

(51) Int. Cl.$^7$ ................................................ B65D 47/10
(52) U.S. Cl. .............................. 222/541.5; 222/541.6; 604/310; 604/257
(58) Field of Search .......................... 222/541.5, 541.6, 222/92, 94, 541.9; 604/257, 294, 217, 132, 204, 198, 110, 310

(56) References Cited

U.S. PATENT DOCUMENTS 4,408,699 A * 10/1983 Stock .......................... 222/149
4,955,871 A * 9/1990 Thomas ........................ 604/217

* cited by examiner

Primary Examiner—Brian L. Casler
Assistant Examiner—Kevin C. Sirmons
(74) Attorney, Agent, or Firm—Hoffman & Baron, LLP

(57) ABSTRACT

A controlled-dose dispenser is useful to provide drops of liquid substances such as drugs, vaccines, ophthalmic solutions or other fluid solutions. The dispenser includes a body preferably made from two sheets of plastic material that are thermoformed in face-to-face relationship. A portion of the body is generally flat with a reservoir, which preferably is generally rounded, in a central portion. The reservoir is adapted to contain a chosen liquid substance. An outlet port is in fluid communication with the reservoir. An outlet nozzle is secured to the outlet port. A cap portion seals off the end of the outlet nozzle until a breakable or frangible connection is broken to remove the cap portion. Once the cap portion is removed, the liquid substance within the reservoir can be dispensed through the nozzle and the cap portion preferably cannot be replaced so that the dispenser is especially suited to be a single-use device.

13 Claims, 2 Drawing Sheets

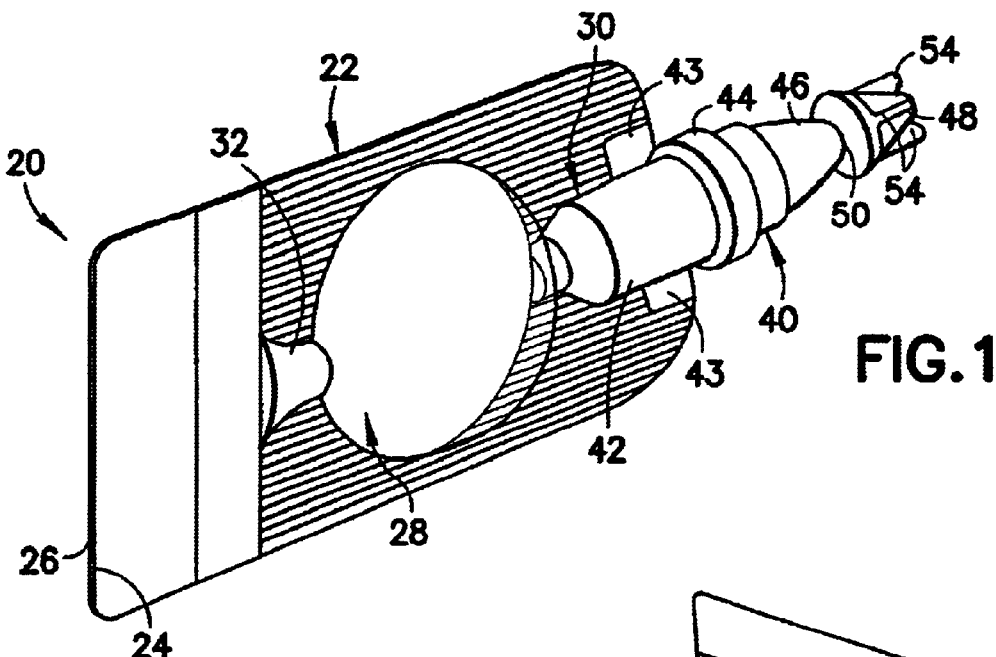
FIG. 1
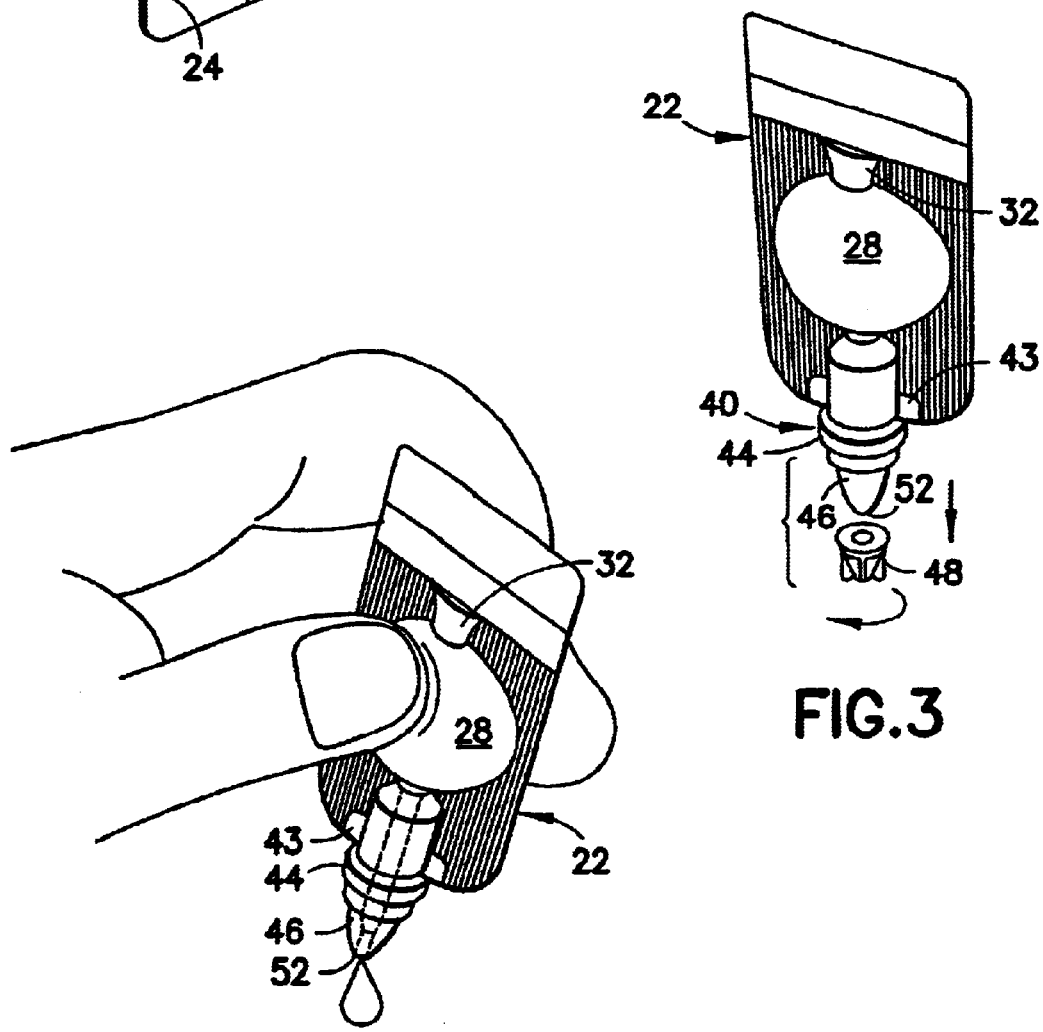
FIG. 3
FIG. 4

CONTROLLED-DOSE DISPENSER WITH INTEGRAL NOZZLE AND CAP

RELATED APPLICATION

The subject application is a continuation of U.S. Ser. No. 09/417,344, which was filed on Oct. 14, 1999, and is entitled "Controlled-Dose Dispenser with Integral Nozzle and Cap".

FIELD OF THE INVENTION

The present invention generally relates to dispensers and, more particularly, to a single-use dispenser for supplying a desired dosage of a liquid substance such as a drug, vaccine, ophthalmic solution and the like in drop form for delivering, including ophthalmic, oral, nasal or ear use or to irrigate a wound or the eyes, for example.

BACKGROUND OF THE INVENTION

A variety of disposable medication dispensers are available on the market. Some are designed for single use, while others are intended for multiple dosage. Some dispensers are intended for hypodermic injection while others are droppers that provide liquid drops to be placed into an individual's eyes or ingested through the mouth, for example.

Multiple dose droppers typically include a bottle with a screw-on cap that is removable whenever some of the solution is needed. One disadvantage associated with such multiple-use caps is that sterility of the container cannot be guaranteed once the cap is removed and later replaced. An additional disadvantage of multiple dosage droppers is that the bottle portion typically must be made by one process, such as blow molding, while the dropper tip is typically made with another molding process. These different processes can introduce manufacturing expenses that reduce the desirability of providing such devices on a mass production scale.

Single dose products typically include a reservoir made by a blow-fill-seal process using a polyolefin material. A disadvantage associated with such devices is that they require specialized machinery which introduces expenses that must be recovered and, consequently, results in an increased price for such devices. This is a disadvantage in the current marketplace where cost-savings are critical.

Another significant drawback associated with blow-fill-seal devices is that the medicament must be inserted while the plastic dispenser is still hot. Some substances cannot be subjected to such heat without adversely affecting the efficacy of the medicament. Therefore, blow-fill-seal devices have limited use.

One advance in single-dose technology is shown, for example, in U.S. Pat. No. 4,955,871, which was issued on Sep. 11, 1990, the disclosure of which is hereby incorporated by reference in its entirety. The device of that patent provides a single-use hypodermic dispenser. The reservoir for holding the medication prior to the hypodermic injection is made from two sheets of thermoplastic material, which presents cost savings because of a simplified manufacturing process and materials compared to other single-dose designs.

Prior to this invention, none of the conventional technology has been utilized to make a single-dose, dropper-type dispenser that avoids the shortcomings and drawbacks discussed above. This invention fulfills that need and avoids the difficulties associated with prior devices.

SUMMARY OF THE INVENTION

In contrast to the prior devices discussed above it has been found that a disposable, fluid dispenser for use in delivering liquid substances such as drugs, vaccines, ophthalmic solutions and the like can be constructed in accordance with the present invention. Specifically, a dispenser body has two side walls that are at least partially joined together in face-to-face relationship to form relatively flat portions of the body. A reservoir portion is formed by generally flexible portions of each side wall that are spaced from each other. The body includes an outlet port in fluid communication with one side of the reservoir. An outlet nozzle has a first end that is secured to the outlet port. The outlet nozzle length may vary to accommodate different applications of the dispenser. A cap portion closes off the opposite end of the nozzle. The cap portion preferably is integrally formed with the nozzle and has a connection with the outlet nozzle such that the cap portion can be manually removed from the outlet nozzle to selectively allow fluid to be expelled from the reservoir through the outlet nozzle.

In the preferred embodiment, the connection between the cap portion and the outlet nozzle is breakable such that twisting, pulling or bending the cap portion with sufficient force breaks the cap portion off of the outlet nozzle. When the cap portion is broken off, the nozzle opening is exposed to allow the fluid from the reservoir to be expelled from the outlet nozzle. The cap portion preferably includes a plurality of projections that facilitate handling the cap portion and removing it from the outlet nozzle.

The various features and advantages of this invention will become apparent to those skilled in the art from the following detailed description of the currently preferred embodiment. The drawings that accompany the detailed description can be briefly described as follows.

BRIEF DESCRIPTION OF THE DRAWINGS

FIG. 1 is a diagrammatic illustration of a dispenser designed according to this invention;

FIG. 3 illustrates a method of removing the cap portion from the outlet nozzle of the embodiment of FIG. 1; and FIG. 4 illustrates the dispenser in use.

DETAILED DESCRIPTION OF THE PREFERRED EMBODIMENT

Figure 2A:
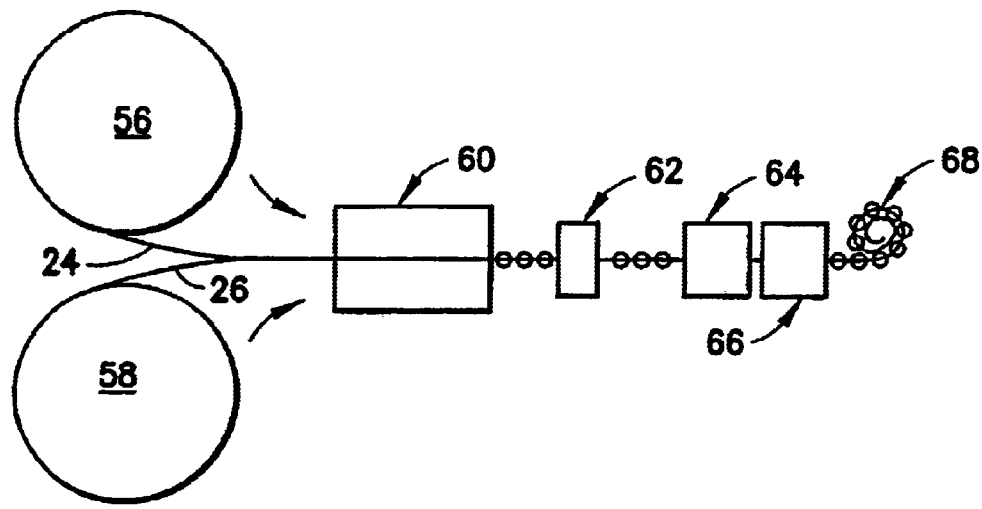
FIGS. 2A and 2B schematically illustrate a method of making dispensers designed according to this invention.

FIG. 1 diagrammatically illustrates a dispenser 20, which preferably is utilized to dispense drops of a liquid substance such as a drug, vaccine, ophthalmic solution or the like. The dispenser 20 can be utilized in situations where eye drops, nose drops, or ear drops are needed. Additionally, the dispenser 20 is conveniently used for taking substances orally, particularly drugs and vaccines. The currently preferred embodiment of the dispenser 20 is intended for single use applications where drops of a liquid substance are needed.

The dispenser 20 includes a body portion 22 that preferably is made from two sheets of thermoplastic material 24 and 26. Each sheet of material preferably is made from multiple layers. An inside layer preferably is chosen to be made from a thermoplastic material that will not have any adverse effect on or reaction with the liquid substance that will be provided in the dispenser 20.

The majority of the outer periphery of the body portion 22 preferably is flat with a center reservoir 28 that is preferably generally rounded. An outlet port 30 is in fluid communication with one end of the reservoir 28. An inlet port 32 is in fluid communication with an opposite side of the reservoir 28. An outlet nozzle 40 has a first end 41A and a second end 41B and includes a first or port portion 42 that is received within the outlet port 30 of the body 22 at the first end 41A, with the port portion having a first outer diameter. Tabs 43 also preferably are secured between the two sheets 24 and 26 for added structural integrity. The port portion 42 and tabs 43 preferably are secured to the body 22 and the outlet port 30 using a conventional heating or plastic welding technique.

The nozzle 40 includes a midportion or a flange 44 that has a second outer diameter greater than the first outer diameter and that is received adjacent an edge on the body portion 22. The flange 44 provides structural integrity to the dispenser 20 because of its increased size relative to the port portion 42. A dispenser or outlet portion 46 extends from the flange 44 and is connected to a cap portion 48.

The outlet portion 46 and the cap portion 48 preferably are integrally formed during a single molding process. The cap portion 48 and the outlet portion 46 most preferably are connected with a breakable or frangible connection 50. The nozzle and cap portion most preferably are made from a polyethylene material to ensure that no extractables adversely impact the liquid substance in the reservoir 28. The cap portion 48 preferably includes at least two wing portions 54 that facilitate grasping the cap portion 48 and manipulating it relative to the remainder of the nozzle 40 to remove it as desired.

Figure 2B:
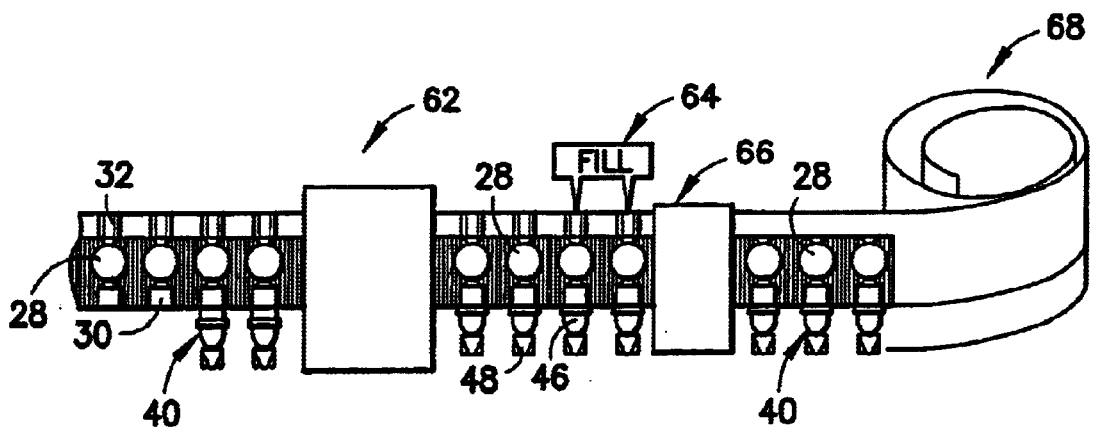

FIGS. 2A and 2B schematically illustrate the preferred method of making a plurality of the dispensers 20 using an automated process. FIG. 2A overviews the entire process. FIG. 2B shows selected portions of the process in more detail. Two rolls 56, 58 of elongate sheets of thermoplastic material 24 and 26 preferably are fed into a mold 60 that forms the body portions 22 of each dispenser 20. The mold 60 can include heating, vacuum forming, or other pressure molding techniques as known in the art to secure portions of the sheets 24 and 26 together to form the relatively flat portions of the body 22. The reservoir 28 preferably is formed by expanding appropriate portions of the sheets 24 and 26 using air pressure to form a generally rounded pocket or reservoir 28 approximately in the center of the body portion 22.

After the molding portion of the process is complete, the body portion 22 includes the reservoir 28, the outlet port 30 and the inlet port 32. The strip of dispensers 20 preferably are not separated into individual units until a later time. The molding portion of the process may include perforating the strip between the respective body portions to facilitate later separation.

The nozzle 40 preferably is preformed using an injection molding or a gas injection molding process. The cap portion 48 most preferably is integrally molded with the nozzle portion. The nozzle 40 is then secured to the outlet port 30 using a conventional heating or plastic molding technique (schematically shown at 62). At this point, each cap portion 48 closes off the outlet port 30 of each reservoir 28.

Next, the dispenser 20 preferably is filled with a desired substance (schematically shown at 64) which can be a drug, vaccine, ophthalmic solution or other liquid, depending on the needs of a particular situation. Once the reservoir is filled with a desired amount of the liquid substance, the inlet port 32 preferably is sealed closed using a conventional plastic welding technique at 66. Then the strip of dispensers 20 preferably are wrapped on a reel at 68. At this point, the dispensers 20 are ready for packaging and shipping as desired.

In most instances, it is desirable to maintain sterility of the liquid substance within the dispenser 20. The liquid substance and the internal, fluid-contacting surfaces of the dispenser need to be sterile.

Sterilizing empty dispensers can be performed off-line in a conventional batch process, after they have been completely assembled (including nozzles), formed into a reel and packaged. The preferred method for sterilizing the completely packaged reel is irradiation. This approach is typically used in circumstances where it is useful to make the dispenser at one location and then fill it at another. In these situations, it is preferred to form the dispensers, sterilize entire cartons of dispensers, and then ship the sterilized dispensers to a pharmaceutical company to be filled, sealed, and repackaged for shipping.

An alternative approach is to form, assemble, and fill the dispensers in one integrated, continuous process. This results in a much lower cost, higher efficiency operation. In this case, the dispensers are sterilized on-line after thermoforming and prior to filling. In one embodiment, the two sheets of film would be sealed together and thermoformed, followed by rapid, on-line sterilization of the films, insertion and heat sealing of presterilized nozzles, aseptic filling of presterilized liquid, and sealing. The preferred methods of on-line sterilization in this case are high intensity pulsed light or electron beam radiation. The nozzles preferably are presterilized by irradiation. The liquid preferably is presterilized by filtration through microporous 0.22 micron or 0.1 micron filters.

In another embodiment, the sheets of film are sealed together and thermoformed followed by inserting and heat sealing nonsterile nozzles. A rapid, on-line sterilization of the assembled dispenser, aseptic filling of presterilized liquid, and sealing preferably follow in that order. The preferred method of on-line sterilization in this case is electron beam radiation. High intensity pulse light is not an alternative because the wall thickness of the injection molded nozzle will interfere with light penetration.

For liquid products that can withstand elevated temperatures, an alternative to sterile filtration and aseptic filling is terminal sterilization of the liquid after it has already been filled in the dispenser. This can be done off-line in a batch process, using irradiation. The conventional autoclave sterilization method is not possible for the preferred materials of the dispenser (polyethylene), but would be possible if polypropylene or other materials were used. Alternatively, an on-line continuous process could be used to terminally sterilize the liquid. Preferred methods include high intensity pulsed light, electron beam radiation, or microwave. In some cases, the irradiation techniques can be used to sterilize the dispenser at the same time as terminally sterilizing the filled liquid, which eliminates the need for presterilizing the dispenser prior to filling.

Once filled, the dispenser 20 preferably includes the exact amount of the liquid substance intended for a single dosage or single application. The connection 50 between the cap portion 48 and the outlet nozzle 46 preferably is breakable or frangible. As shown in FIG. 3, twisting, pulling or bending the cap portion 48 relative to the remainder of the nozzle 40 results in the connection 50 being broken.

Once the cap portion 48 is removed, an opening 52 is exposed through which the liquid substance within the reservoir 28 can be dispensed. After the cap portion 48 has been removed, an individual simply presses upon the outer walls of the reservoir 28 to dispense the liquid substance through the opening 52 of the outlet nozzle 46.

This invention most preferably provides a single-use device because the cap portion 48, once removed, preferably cannot be replaced. The preferred embodiment is provides the advantage of maintaining sterility when desired since a sterile liquid substance and nozzle cannot be guaranteed once a cap is removed and then later replaced. A further advantage provided by this invention is that the liquid substance is more accurately dispensed because the thermoplastic sheets 24 and 26 preferably are transparent, which makes it easier to see exactly how much liquid substance is in the reservoir 28 and to confirm that the entire contents have been dispensed as desired.

The dispenser 20 also is a single-use device in that it cannot be readily refilled, which discourages re-use. This feature preferably is accomplished by providing sidewalls for the reservoir 28 that collapse into each other when the liquid substance is dispensed. When the reservoir walls do not return to their formed shape, reusing the reservoir 28 becomes highly impractical.

The volume contained within the reservoir 28 can be varied depending on the needs of a particular situation. Additionally the size of the opening 52 on the outlet nozzle 46 can be varied to result in different sized drops. The size requirements for the opening relative to the desired drop size will vary depending on the nature and viscosity of the liquid substance. The size of the opening required can be determined using the following formula:

$$V_0 = 2\pi_g y/pg;$$

where, the $V_0$ is the volume of slowly formed drops, $2\pi_g$ is the effective circumference of the opening 52, y is the surface tension of the liquid substance, p is the specific gravity of the liquid substance, and g is the gravitational pull.

In situations where rapidly formed drops are desired, the following formula can be used:

$$V_r = V_0 + f(r);$$

where r is the rate of desired flow. Those skilled in the art will be able to determine appropriate nozzle opening sizes for a given liquid substance.

The connection 50 preferably is a reduced neck portion or region that has a third outside diameter smaller than the second outside diameter of the flange 44 and is frangible or breakable when sufficient force is applied. The cap portion 48 has an outer diameter that is larger than a third outside diameter and which closes off the second end 41B of the nozzle 40. It is important that the cap portion 48 remain in place during shipping and normal handling to maintain the fluid within the reservoir 28 and to maintain sterility as needed. The connection 50 preferably has a reduced material thickness compared to the adjacent portion of the outlet nozzle 46, i.e., between the inside opening 52 and the outside surface. The reduced neck can be accomplished by reducing the outside diameter of the assembly immediately adjacent the cap portion 48. Alternatively, expanding the inside diameter of the nozzle portion 46 immediately adjacent the opening 52 provides a reduced material thickness at the connection 50. The exact dimensions required will vary depending on the material utilized in a particular situation. Given this description, those skilled in the art will be able to determine sufficient geometries and dimensions to realize the results provided by this invention.

This invention provides a dispenser 20 that is far more economical to manufacture compared to conventional single-use and multiple-use fluid drop dispensers. The unique combination of the body 22 and nozzle portion 40 having the removable cap portion 48 with the breakable connection 50 provides an arrangement that is more economically manufactured than other devices. An integrated molding and filling process can prove especially advantageous. Additionally, this invention provides the advantages of having a relatively transparent reservoir 28, which facilitates visually verifying the amount of liquid substance within the reservoir before and after dosage delivery.

Additionally, the manufacturing requirements for a dispenser designed according to this invention enables a variety of dosage volumes to be accommodated within the reservoir 28 by simple modification of the molding process described above. For example, parts of the mold 60 could be replaced to achieve a different size for the reservoir 28. Alternatively, modifications to a pressure-molding vacuum-molding portion of the manufacturing process can be made to adjust how much the material expands to form the reservoir 28.

The dispenser of this invention provides an economical device that makes orally dispensing medications or vaccines much easier. For example, children may carry a single dose of a needed medicine to school and take the medicine as needed. The dispenser of this invention preferably includes an elongated nozzle when oral administration is intended.

The description just given provides details regarding an example implementation of this invention. Variations and modifications may become apparent to those skilled in the art that do not necessarily depart from the basis of this invention. The scope of legal protection given to this invention can only be determined by studying the following claims.

What is claimed is:

1. A disposable fluid dispenser for retaining and subsequently dispensing a fluid, said dispenser comprising:

a dispenser body having two side walls made from two sheets of thermoplastic material with said side walls being at least partially joined together in facing relationship to form relatively flat portions of said body, said side walls including generally flexible portions which define a generally rounded center reservoir portion formed between said side walls for retaining the fluid;

an outlet port formed within said body between said side walls and in fluid communication with said reservoir;

an inlet portion formed within said body between said side walls and in fluid communication with said reservoir, whereby said inlet port is sealed by securing said side walls together in facing relationship along said inlet port after the fluid is deposited into said reservoir;

an outlet nozzle having a first end and a second end with said first end being secured to said outlet port and in fluid communication with said reservoir, and said second end including a neck portion having a reduced diameter fluid path compared to a remainder of said outlet nozzle for controlling the dispensing of the fluid through said outlet nozzle such that fluid may only be dispensed through said neck portion upon compression of said flexible portions of said reservoir;

a cap portion selectively connected to said second end of said outlet nozzle to provide a closure for said reservoir, and said cap portion having a frangible connection with said neck portion of said outlet nozzle such that said cap portion may be removed from said outlet nozzle to define a fluid passageway through said outlet nozzle for dispensing the fluid from said reservoir through said reduced diameter fluid path of said neck portion upon compression of said flexible portions of said reservoir.

2. The dispenser of claim 1, wherein the frangible connection permits the cap portion to be selectively removed from and subsequently placed on the outlet nozzle.

3. The dispenser of claim 2, wherein the cap portion is removed by twisting and snapping the cap portion thereby breaking the frangible connection.

4. The dispenser of claim 1, wherein a flange extends from the outlet nozzle, and the outlet nozzle includes a port portion that is received within the outlet port of the dispenser body and from the first end of the outlet nozzle to the flange with at least two tabs secured between the two side walls for added structural integrity.

5. The dispenser of claim 4, wherein the port portion and the tabs are secured to the dispenser body and the outlet port using a conventional heating or plastic welding technique.

6. The dispenser of claim 1, wherein a flange extends from the outlet nozzle and the outside diameter of the flange of the outlet nozzle is larger than an outside diameter of said neck portion of said outlet nozzle.

7. The dispenser of claim 6, wherein the cap portion has an outside diameter that is larger than the outside diameter of said neck portion and at least two wing portions that facilitate grasping the cap portion to remove the cap portion from the outlet nozzle.

8. The dispenser of claim 1, wherein the frangible connection has a reduced wall thickness relative to an adjacent portion of the outlet nozzle.

9. The dispenser of claim 1, wherein the dispenser body is made from two sheets of transparent thermoplastic material and each sheet is made from a plurality of layers.

10. The dispenser of claim 9, wherein the outlet nozzle and the cap portion are integrally formed during a single molding process and are made from a polyethylene material.

11. The dispenser of claim 1, wherein the reservoir contains a vaccine that is to taken orally.

12. The dispenser of claim 1, wherein the reservoir contains an ophthalmic solution.

13. The dispenser of claim 1, wherein the reservoir contains a liquid substance that is to be administered to an individual.

* * * * *

UNITED STATES PATENT AND TRADEMARK OFFICE
CERTIFICATE OF CORRECTION

PATENT NO. : 6,666,359 B2
DATED : December 23, 2003
INVENTOR(S) : Lau et al.

It is certified that error appears in the above-identified patent and that said Letters Patent is hereby corrected as shown below:

Column 5,
Line 1, delete "...embodiment is provides..." and insert -- embodiment provides --.

Column 8,
Line 15, delete "...that is to taken orally..." and insert -- that is to be taken orally --.

Signed and Sealed this

Thirteenth Day of April, 2004

JON W. DUDAS
*Acting Director of the United States Patent and Trademark Office*